US006347884B1

United States Patent
Faure et al.

(10) Patent No.: US 6,347,884 B1
(45) Date of Patent: Feb. 19, 2002

(54) METHOD AND DEVICE FOR DETERMINING THE STABILITY OF A WATER-HYDROCARBON EMULSION

(75) Inventors: Yan Faure, Saint Chamond; Jean-Marie Letoffe, Decines; Philippe Schulz, Sainte Foix les Lyon, all of (FR)

(73) Assignee: Elf Antar France, Courbevoie (FR)

( * ) Notice: Subject to any disclaimer, the term of this patent is extended or adjusted under 35 U.S.C. 154(b) by 0 days.

(21) Appl. No.: 09/367,849

(22) PCT Filed: Feb. 26, 1998

(86) PCT No.: PCT/FR98/00374

§ 371 Date: Nov. 12, 1999

§ 102(e) Date: Nov. 12, 1999

(87) PCT Pub. No.: WO98/38489

PCT Pub. Date: Sep. 3, 1998

(30) Foreign Application Priority Data

Feb. 27, 1997 (FR) .............................. 97 02366

(51) Int. Cl.[7] .......................... G01N 25/00; G01N 9/02
(52) U.S. Cl. .......................... 374/45; 73/61.44; 374/14
(58) Field of Search ............... 374/14, 45, 44, 374/141, 46; 73/61.46, 61.44, 433, 30

(56) References Cited

U.S. PATENT DOCUMENTS

| | | | | |
|---|---|---|---|---|
| 3,902,354 A | * | 9/1975 | Harlan et al. ............... 73/15 B |
| 4,589,782 A | * | 5/1986 | Park ............................ 374/14 |
| 4,596,470 A | * | 6/1986 | Park ............................ 374/14 |
| 4,606,649 A | * | 8/1986 | Michail ....................... 374/10 |
| 4,743,357 A | * | 5/1988 | Patel et al. ................. 208/113 |
| 4,817,745 A | * | 4/1989 | Beshoory ..................... 177/212 |
| 5,215,377 A | * | 6/1993 | Sugano ........................ 374/14 |
| 5,321,719 A | * | 6/1994 | Reed et al. ................... 374/14 |
| 5,826,983 A | * | 10/1998 | Nakamura et al. ............ 374/14 |
| 6,076,961 A | * | 6/2000 | Claudy et al. ................ 374/45 |
| 6,127,185 A | * | 10/2000 | Melton et al. ................ 436/60 |
| 6,257,757 B1 | * | 7/2001 | Nakamura .................... 374/14 |
| 2001/0000060 A1 | * | 3/2001 | Toma et al. ................ 73/61.44 |

FOREIGN PATENT DOCUMENTS

| | | | | |
|---|---|---|---|---|
| JP | 406221981 | * | 8/1994 | .................... 374/4 |
| JP | 406229899 | * | 8/1994 | .................... 374/4 |

OTHER PUBLICATIONS

U.S. application No. 09/147,201, Mar. 16, 1999, pending.
U.S. application No. 09/367,849, Aug. 27, 1999, pending.

* cited by examiner

Primary Examiner—Diego Gutierrez
Assistant Examiner—Gail Verbitsky
(74) Attorney, Agent, or Firm—Oblon, Spivak, McClelland, Maier & Neustadt, P.C.

(57) ABSTRACT

The invention concerns a method and device for determining the temperature stability of a water-hydrocarbon emulsion capable of phase separation by monitoring the weight variations of a gravimetric sensor part of which is immersed in said mixture. The method consists in a first step of cooling or heating the emulsion to a predetermined temperature; and a second step during which the emulsion is maintained at this temperature, the time-dependent variation curve of said weight in time enabling the determination of the solid mass collected and the separation speed into two phases by determining the slope of this curve, the stability of the emulsion being obtained by comparison with reference emulsions known to be stable.

10 Claims, 6 Drawing Sheets

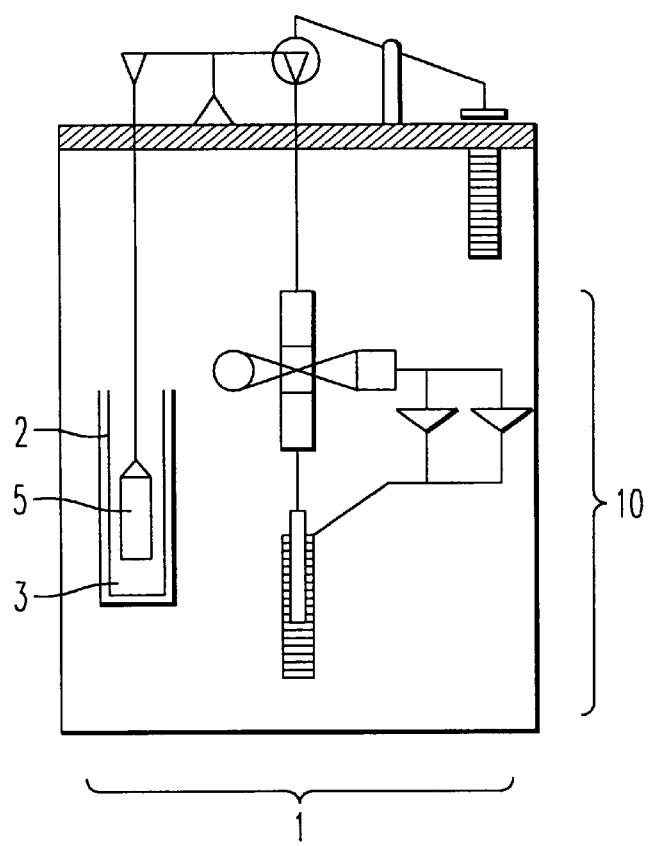
*FIG. 1A*
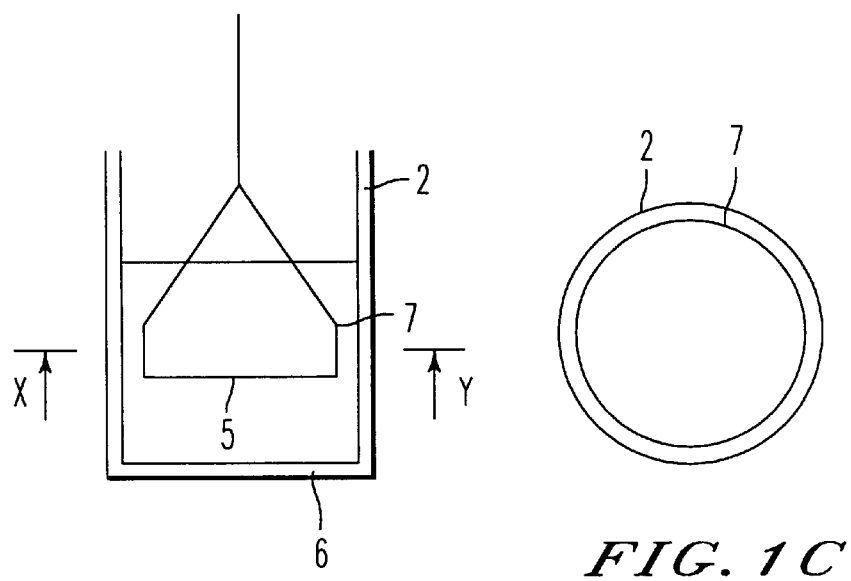
*FIG. 1B*
*FIG. 1C*
SECTION XY

Photo N° 1 : EMUO1

Photo N° 2 : EMUO2

METHOD AND DEVICE FOR DETERMINING THE STABILITY OF A WATER-HYDROCARBON EMULSION

The present invention relates to a process for determining the stability of a water-hydrocarbon emulsion.

This process can be used to determine the stability of a water-hydrocarbon emulsion which is stable at ambient temperature, generally usable as a fuel, which, under the influence of a variation in temperature—cooling or heating—is capable of separating into two or more liquid and/or solid phases on account of demixing or crystallization of the water, followed or preceded by sedimentation of the paraffins in the hydrocarbon matrix.

In the text hereinbelow, the term "emulsion" or "water-hydrocarbon emulsion" will denote, without preference, an emulsion of an aqueous dispersed phase in hydrocarbons and the possible additives thereof constituting the continuous phase, or alternatively an emulsion of hydrocarbons dispersed in an aqueous phase.

It is well known that the presence of a small fraction of water dispersed in a hydrocarbon improves the quality of combustion of this hydrocarbon and substantially reduces the amount of harmful, unburnt and nitrogen oxides emissions, the vaporization of the water resulting in a lowering of the temperature in the combustion chamber. Unfortunately, the immiscibility of the two fluids substantially limits the use of this property to its implementation in burners preparing the emulsion in situ. Attempts to produce fuels and combustion spirits consisting of an emulsion by addition of surfactants to the mixture failed, since they were not sufficiently stable for industrial application. Recent investigations have allowed the formulation of novel fuels whose stability is such that their industrial exploitation appears possible (see patent application WO 97/34969 of Mar. 17, 1997).

This industrial application requires the development of a reliable process for controlling the stability of the emulsions thus manufactured, this process being reliable both over time and under the influence of temperature.

The problem is difficult on account of the complex phenomena which take place in a medium, which is heterogeneous by nature, in particular when it is subjected to variations in temperature.

The reason for this is that crude or refined hydrocarbons contain a larger or smaller proportion of paraffins, which are soluble "under hot conditions" but which, under the influence of a decrease in temperature, can crystallize and then sediment and thus give rise to dysfunctions on storage or during their use. The stability of the emulsion is temperature-sensitive both under hot conditions, since an increase in temperature promotes the demixing phenomenon, and under cold conditions, in which case the crystallization of the free water accelerates the separation process.

Thus, the possibility of providing conditions under which a liquid emulsion, which is initially stable at ambient temperature, can separate into at least two phases under the influence of time and/or temperature is a considerable asset for the optimum use of this emulsion.

The emulsion can be prepared with any hydrocarbon, such as spirits, gas oils, domestic fuel oils or heavy fuel oils, these fuels possibly containing various additives or components known to those skilled in the art, such as oxygenated compounds (alcohols, ethers or methyl esters of plant oil). The same types of problem arise for all the products, particularly products containing paraffins, for which filtration, pumping and blockage problems are observed, in particular in motors and in industrial and domestic heating systems. By analogy, reference will be made to summer or winter emulsion formulations, as common terminology, for domestic fuel oils, summer fuel oil and winter fuel oil according to the specifications in force.

Surfactant additives which facilitate the formation of the emulsion and ensure its stability are added to the water-hydrocarbon mixture to avoid the appearance of the demixing phenomenon. To avoid the crystallization and then sedimentation of the paraffins, during use under cold conditions, additives whose action delays the appearance of the crystals, prevents their development, keeps them in suspension or prevents their sedimentation are added to the emulsions already containing their own additives. It is thus important to measure the impact of these various additives on the phenomena of phase separation of an emulsion.

Various methods exist for measuring the characteristics of appearance and separation of a solid phase in liquid.

A first method is based on measuring the weight of the solids, such as the paraffins in the gas oils which have crystallized at a given temperature. These paraffins are extracted from the hydrocarbon by centrifugation (patent EP-0,355,053 A2) or by aggregation in a gravity sedimenter (U.S. Pat. No. 4,357,244). These tests make it possible only to determine the total amount of paraffins which have crystallized and which can sediment out. They gave a measure of the excess sedimentation.

A second type of test simulates the real-time sedimentation in small tanks (standard NF M 07-085) in which are stored hydrocarbons at low temperature for 24 or 48 hours. The appearance and volume of each phase are then assessed visually by the experimenter, in particular the position of the interface between the two phases. These tests give an approximate qualitative measure of the sedimentation.

Optical methods for measuring the characteristics of appearance of two immiscible-liquid or solid-liquid phases also exist. Mention may be made of patent FR 2,577,319 which is directed towards determining the cloud point of gas oils, and patent FR 2,681,428 which is directed towards the demixing of two liquids (measurement of the aniline point of hydrocarbons).

These methods all have drawbacks and inadequacies:

They are long, since they generally last 24 hours or 48 hours.

They are not reliable, since they depend only on subjectivity of the observer.

Most especially, however, they do not make it possible to measure the amounts of the separated phases, or to know the speed of separation of the phases, or even to explain and quantify the successive states through which the liquid passes when the temperature changes.

The process for determining the stability of a water-hydrocarbon emulsion by thermogravimetric analysis, which is the subject of the invention, solves the problem of the quantitative measurement of the separation of the liquid or solid immiscible phases using a liquid which has been made homogeneous.

A subject of the present invention is a process for determining the stability of a water-hydrocarbon emulsion liable to exhibit a phase separation, characterized in that in a first step, by subjecting the said emulsion to a suitable heat treatment, it is brought to a predetermined test temperature and the variation in the apparent weight P of the gravimetric detector, a portion of which is immersed in the emulsion, is continuously measured by thermoaravimetry, then in a second step, the emulsion is maintained at this temperature while continuously measuring the variation in the apparent weight of the said detector by thermogravimetry, and the curve of the variation of this weight is recorded simultaneously, and then the mass of the separated phase collected, on the one hand, and the speed of separation of the phases corresponding to the slope of the said curve, mainly the speed measured at the breaking point corresponding to a substantial and continuous increase in the apparent weight P at the start of the second step, on the other hand, are determined from the said curve, and the stability of the emulsion is deduced by comparison with known reference emulsions, whose stability over time has been corroborated by tests of long-lasting stability.

The expression "predetermined temperature" means here the steady temperature at which it is desired to measure the stability of the emulsion, but also, for the behaviour under cold conditions, the temperature at which the separation is visible, i.e. detectable to the naked eye or by infrared as described in patents FR 2,577,319 and FR 2,681,428.

The process of the invention will be carried out according to two main variants depending on whether it is directed towards the stability at a predetermined temperature above that of the crystallization of water or, exceptionally, of certain heavy paraffins (behaviour under hot conditions), or the stability at a predetermined temperature which is below the crystallization temperature of at least one of the constituents behaviour under cold conditions). The profiles of the curves for the variation in the apparent weight of the detector as a function of time and of temperature show substantial differences in the duration of the various steps whether the stability of the emulsion is monitored under hot or cold conditions.

The reason for this is that the stability under hot conditions leads to a first step whose duration is associated with the difference in temperature between the temperature of the emulsion prepared, i.e. generally close to ambient temperature, and the test steady temperature. If the test is carried out at ambient temperature, this duration can be zero. If the test temperature is greater than the initial temperature of the emulsion, the latter will have to be heated. On the other hand, the second step, which is complete when the variation in weight becomes zero (i.e. when the phases are completely separate), can be very long, especially if a particularly stable emulsion is tested. In this case, the speed of separation will be the predominant factor to be taken into account.

In order to assess the temperature behaviour of the emulsions, the predetermined test temperature is between 10 and 70° C., the emulsion being brought to this temperature at a heating or cooling speed, from ambient temperature, generally of between 0.05 and 10° C./min.

The determination of the stability of an emulsion at low temperature consists in monitoring the crystallization and sedimentation of water, on the other hand, and of the paraffins, on the other hand, in an emulsion.

In a first embodiment, the first step consists in gradually lowering the temperature at a speed generally of between 0.05 and 10° C./min to between the crystallization temperatures of the water and of the paraffins, while continuously recording the variation in the apparent weight of the detector. This weight decreases on account of the increase in the density of the emulsion. During the second step, the change in the apparent weight of the detector is recorded, while keeping the temperature constant. This weight remains substantially constant up to the point of crystallization of one or other of the two phases depending on whether the crystallization temperature of water is less than or greater than that of the paraffins.

In a second embodiment, the first step consists or gradually lowering the temperature at a speed generally of between 0.05 and 10° C./min down to a predetermined temperature which is less than the crystallization temperatures of the paraffins and of water but greater than the flow temperature of the hydrocarbon-based mixture.

The advantages of the process, which is the subject of the invention, are the precision, reliability and reproducibility of the results obtained, both for assessing the speed of separation of the phases and for measuring the weight variations of the separated phases.

A subject of the present invention is also a device for measuring the separation of an emulsion into several liquid and/or solid phases, comprising a thermogravimetric balance fitted with a gravimetric detector, the portion of which immersed in a tank (2) containing the said emulsion is a crucible (5), the said tank being connected to a cooling circuit, the said device being characterized in that the crucible is free, preferably coaxial with the tank whose cylindrical cross section is such that the ratio of the largest diameter of the crucible to the diameter of the tank is between 0.1 and 0.9.

The crucible has a cylindrical shape comprising a base and rims, the height of which does not exceed the level of liquid in the tank. The height of the rims is between 0.5 mm and 30 mm and generally equal to 5 mm.

The characteristics of the present device will become more apparent on examination of FIGS. 1A, 1B and 1C and the description thereof below.

The device represented in FIG. 1A comprises a thermogravimetric beam balance (1) (of SETARAM type), a tank (2) containing the macroscopically homogeneous liquid mixture (3) to be studied, a temperature control device (not represented in the diagram) for cooling or heating the tank and a computer system (not represented in the diagram) for recording and processing the data.

The beam (4) of the balance (1) carries, suspended on the left arm in the diagram, a crucible (5) immersed in the tank (2) containing the mixture. The tank (2) has a jacket (6) and allows the temperature of the mixture to be modified, by means of a heating or cooling circuit, not represented in the diagram.

The crucible (5) has a cylindrical shape, like the tank, and comprises a base and rims (7).

A standard optical and magnetic system (10), combined with the balance, allows the variations in the weight of the crucible to be measured and recorded.

FIGS. 1B and 1C show the details of the crucible.

The characteristics and advantages of the process of the present invention will emerge more clearly on reading the examples for carrying out the process which are given below, in a non-limiting manner, with reference to FIGS. 2 to 5.

Figure 6:
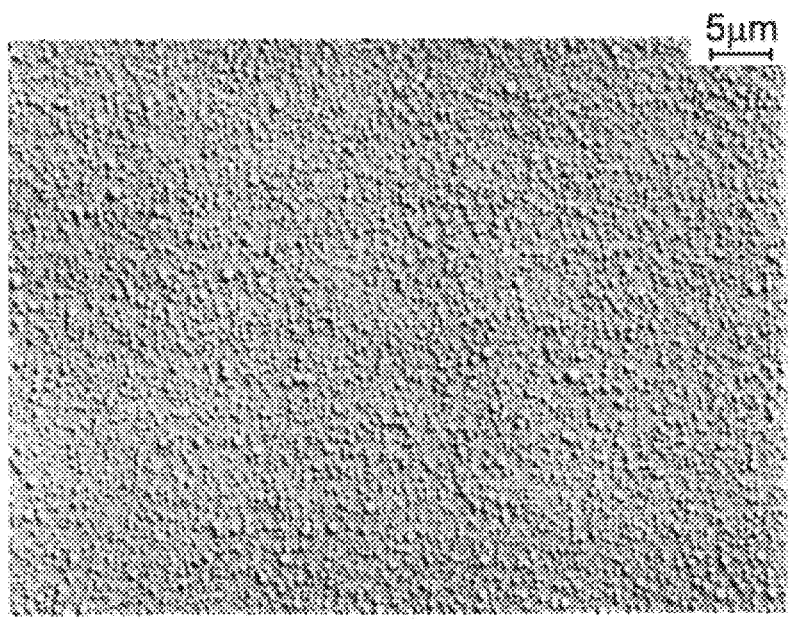
Figure 7:
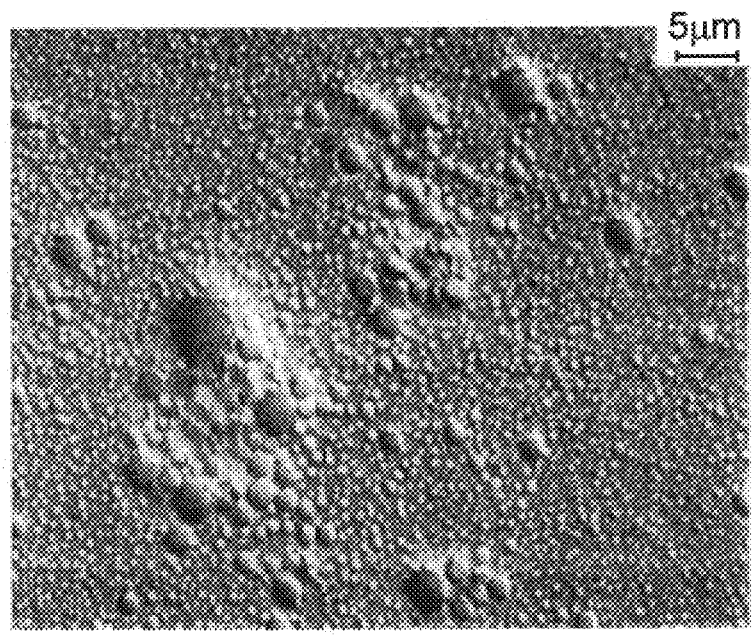

FIG. 6 shows a photograph of emulsion EMU01.
FIG. 7 shows a photograph of emulsion EMU02.

EXAMPLE 1

The present example describes the use of the process of the invention for determining the stability under cold conditions of a water-gas oil emulsion, of winter formulation.

The emulsion is brought to a temperature below the crystallization temperatures of water and of the paraffins, but, needless to say, above the flow point, and the crystallization and sedimentation of the water, on the one hand, and of the paraffins, on the other hand, are monitored.

The process is carried out as follows:

A B60 or TGA 92 model of thermogravimetric balance, with electromagnetic compensation, sold by SETARAM is used. The crucible is a dish 20 mm in diameter with rims 5 mm in height. It is placed in a cylinder 30 mm in diameter and 100 mm in height containing the gas oil to be tested.

The crucible is immersed in the tank to 33 mm below the surface of the gas oil. The temperature of the emulsion is then lowered to −7.5° C., at a speed of 0.7° C. per minute, at which temperature the formation of crystals is visible, and the tank is then kept at this temperature for eighteen hours.

The variations in the relative weight of the crucible during lowering of the temperature and during the steady temperature are recorded. A decrease in the relative weight of the crucible is thus observed, due solely to the variations in the density of the emulsion, which increases as the temperature decreases, followed by an increase in the relative weight, due to the water and paraffins which sediment in the crucible.

The gain $G_P$ in weight of the crucible due to the paraffins and/or the water sedimented is obtained by subtracting, at each instant, the relative weight $P_s$ of the device measured at the start of the second step (constant temperature), from the weight P of the detector measured at time t: $G_P = P - P_s$. The total weight gain is thus the difference in the apparent weight of the device between the end and the start of the second step.

Figure 2:
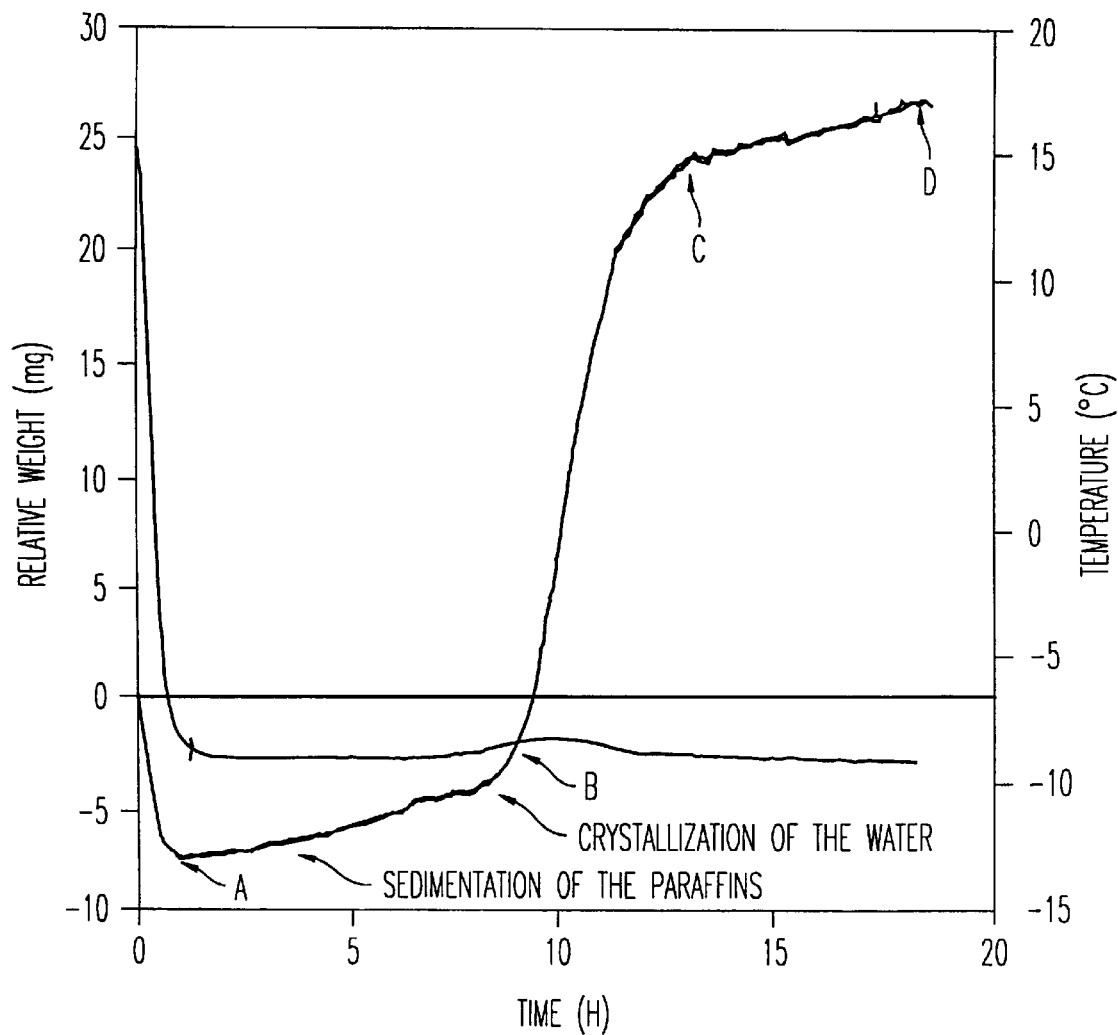
FIGS. 2 to 5 show, in the form of curves, the results of the measurements obtained on various examples of separation of phases.

The curve recorded is that of FIG. 2:

The first portion of the curve is explained by an apparent loss of relative weight, due to the increase in density of the gas oil during the reduction of the temperature (OA).

A latency time is then observed, in which the relative weight increases only slightly (AB) due to the sedimentation of the paraffins alone, the water exhibiting a supercooling phenomenon.

The third portion (BC) reflects a rapid increase in the relative weight, corresponding to the weight of the paraffins and water being deposited at the surface of the crucible during the stationary phase in which the temperature is maintained at −7.5° C. (±0.2° C.).

In the fourth portion (CD), the curve shows a break D, from which point the gain in relative weight is due solely to the sedimentation of the paraffins. Since the water has totally sedimented out, visual observation made at that moment shows a separation of phases.

A prolongation of the test would show on the curve, beyond the point D, a break from which point the gain in relative weight is zero. There is thus no further sedimentation on the crucible, the relative weight measured remaining substantially constant. In practice, this is not useful since precipitation of the free water establishes the instability of the emulsion.

The sedimentation curve in FIG. 2 makes it possible to define three characteristics:

1/ The gain in relative weight (Gp) in milligrams, which represents the total amount of water and paraffins sedimented during the experiment.

2/ The speed of sedimentation (V) of the emulsion in mg per hour, established from the slope of the curve in its portion BC at its point of inflection. This sedimentation speed thus makes it possible to compare different emulsions.

3/ The latency time in hours, which represents the time corresponding to the steady stage AB of the curve, during which the emulsion remains stable at the test temperature.

In the case of the emulsion tested with the curve in FIG. 2, it can be seen that the latency time is 8 hours.

EXAMPLE 2

In this example, another winter-formulation emulsion comprising paraffins which crystallize at lower temperature is analysed, by addition of additives with specific behaviour under cold conditions, the first step being stopped at −8.5° C. before crystallization of the paraffins, i.e. above the cloud point. Only the water crystallizes.

Figure 3:
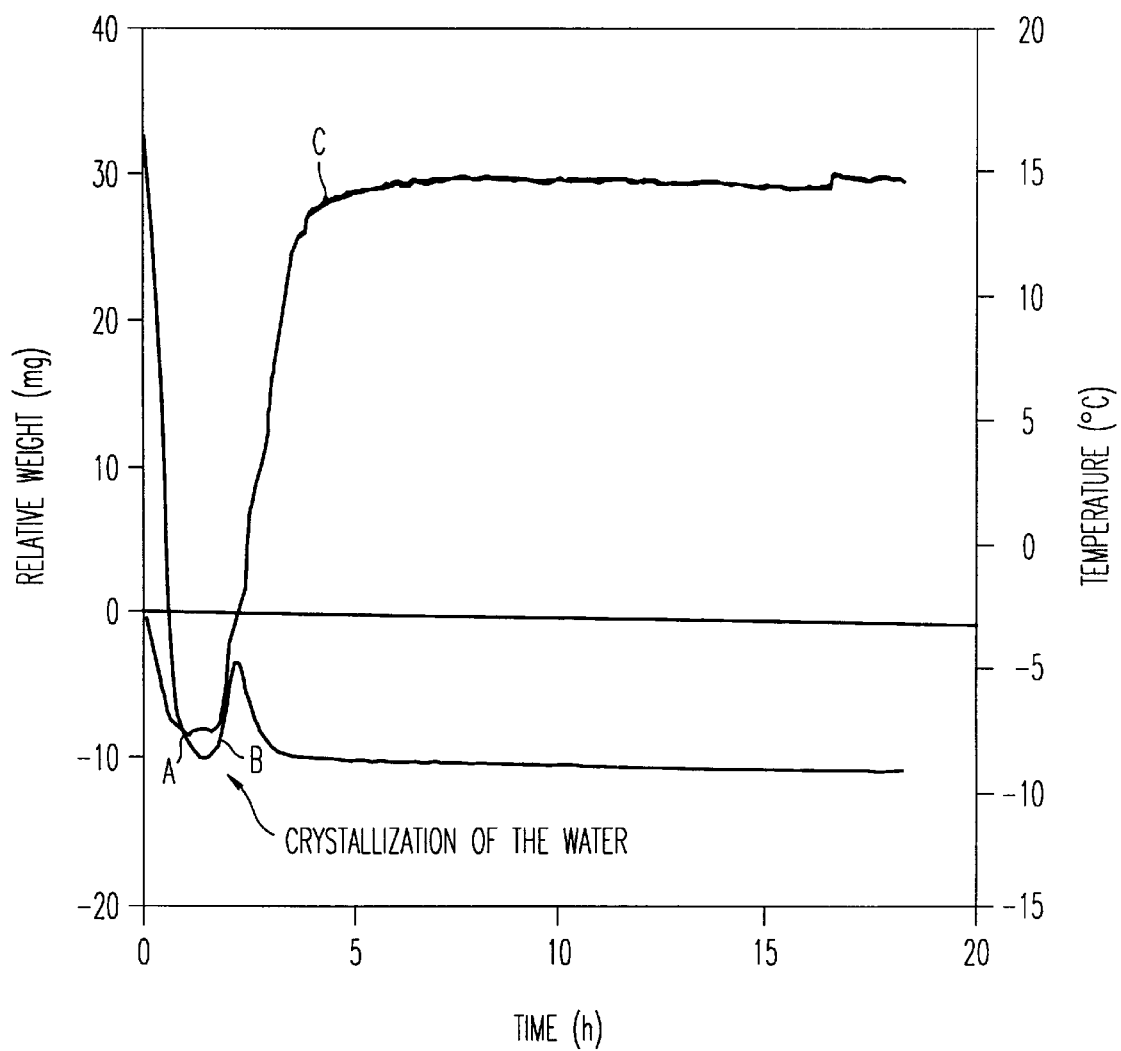

Recording of the variation in weight gave the curve in FIG. 3.

After the decrease in the relative weight of the crucible (OA), a latency period (AB) can be seen, due to supercooling of the water, and finally a very rapid weight gain (BC) due to crystallization of the water. Beyond C, the weight gain becomes zero, since all the water has crystallized. The temperature profile of the medium is characteristic of the phenomenon with the peak due to the exothermic crystallization of water.

The device thus makes it possible to accurately distinguish each of the thermal events experienced by the water-gas oil emulsion, and to quantify the level of separation by measuring the sedimentation speeds and the apparent weight gain.

EXAMPLE 3

This example illustrates the determination, according to the process of the invention, of the stability at ambient temperature (20° C.) of two emulsions EMU01 and EMU02 obtained by mixing 13% by weight of water in a gas oil of type EN590, containing specific additives for emulsion maintenance and in which the particle size distributions of the water droplets in the gas oil are very different:

The emulsion EMU01 has a monodisperse particle size distribution with drop diameters centred about 1 μm (see photograph 1 in FIG. 6).

The emulsion EMU02 has a less well dispersed aqueous phase referred to as a polydisperse phase, with drop diameters ranging from 0.1 μm to 50 μm (see photograph 2 in FIG. 7).

Figure 4:
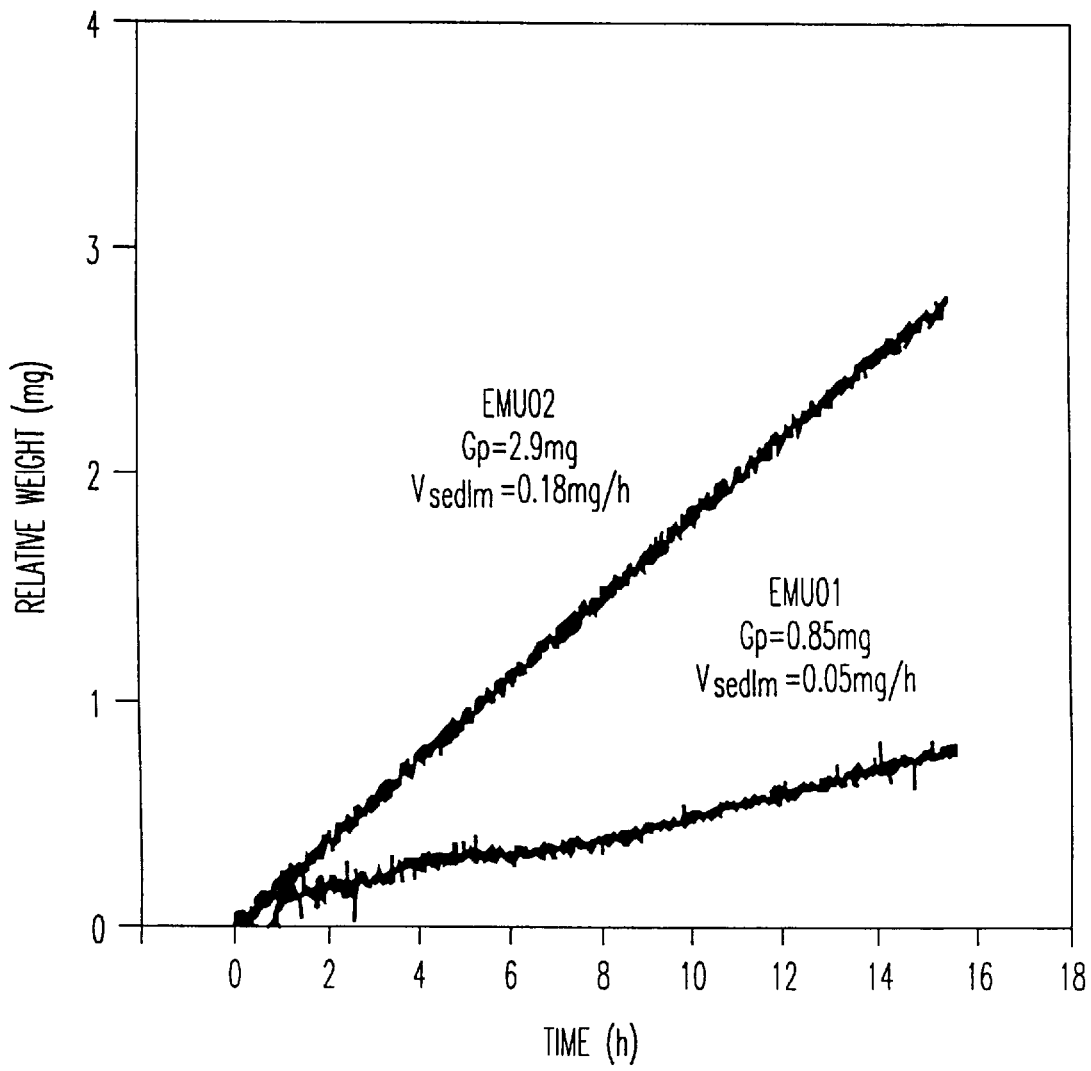
Figure 5:
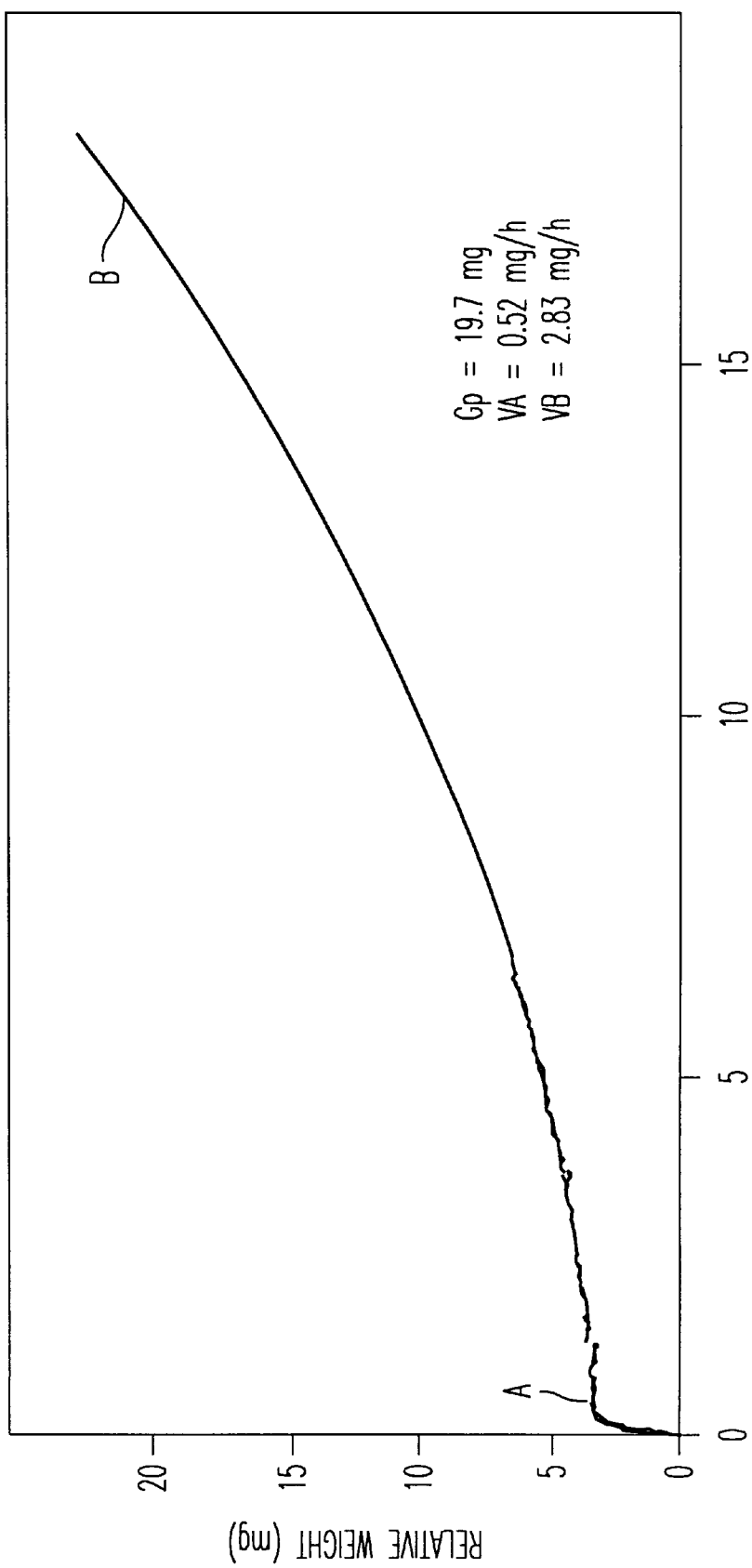

Recording of the apparent weight increase allowed the curves given in FIG. 4 to be established. In this case, the steady temperature (20° C.) is greater than the crystallization temperature of water and of the paraffins. A linear change of the increase in relative weight with time is obtained. The two main parameters (V and Gp) are markedly higher for the emulsion EMU02, which is thus less stable than the emulsion EMU01. Since the sample EMU01 shows a more homogeneous dispersion of water in the continuous phase, it will have less of a tendency to flocculate and sediment. This example clearly shows that it is possible, by means of the process according to the invention, to establish a quantitative scale of the stability of the emulsions manufactured by comparison with a tested reference and at a given temperature. In addition, the particle size analysis by image processing gives only a local analysis, which, although possibly being statistically analysable, is long and complex, while the process according to the invention allows a global analysis on the entire volume of the sample, irrespective of the temperature, without having to dilute the sample.

EXAMPLE 4

This example is aimed at showing that the process according to the invention makes it possible to qualify and optimize an industrial emulsion manufacturing process. Specifically, various emulsions were prepared industrially in a closed-circuit plant comprising an emulsion mill and a sample outlet to allow samples to be taken after a certain number of recycling operations or runs. The stability of these samples at ambient temperature is measured by the process according to the invention under the conditions described in Example 3, and is compared with the stability of an EMU reference emulsion containing 13% water, referred to hereinbelow as the REFERENCE, the stability of which was checked over a long period. This REFERENCE was prepared in the laboratory so as to obtain a monodisperse particle size distribution of the water droplets centred about 1 μm, this distribution having been analysed by electron microscopy and image processing.

A certain amount of gas oil EN590 and 13% by weight of water, relative to the amount of gas oil, the mixture being emulsified (EMU03), are introduced into the closed circuit of the industrial plant.

Samples were taken after 4 and 7 recirculation runs of the mixture. The emulsions were analysed by the process according to the invention. The apparent weight gains and the sedimentation speeds after 1 hour ($V_1$) and 6 hours ($V_2$) were measured: they are collated in Table 1.

TABLE 1

| | T = 20° C. | | |
|---|---|---|---|
| | Gp (mg) | $V_1$ (mg · h$^{-1}$) | $V_2$ (mg · h$^{-1}$) |
| REFERENCE | 3.1 | 0.11 | / |
| EMU03 4 runs | 13.9 | 0.12 | 2.0 |
| EMU03 7 runs | 3.8 | 0 | 0.4 |

It can clearly be seen that it is possible to control the stability of an emulsion in order to modify the manufacturing process so as to reach the reference level.

EXAMPLE 5

In this example, the stability of two emulsions EMU04 (summer formulation) and EMU05 (winter formulation) was studied as a function of the predetermined temperatures (between 40° C. and −8° C.), working as described in Examples 1 and 3 for the temperature increase or decrease during the first step of the process of the invention. The results obtained are collated in Table 2 below:

TABLE 2

| | V (mg · h$^{-1}$) | | | | | | | | |
|---|---|---|---|---|---|---|---|---|---|
| Temperature | 40° C. | 30° C. | 20° C. | 10° C. | 0° C. | −4° C. | −7° C. | −8° C. | −9° C. |
| EMU01 | 0.24 | 0.12 | 0.11 | 0.08 | 0.06 | — | — | — | — |
| | 4.5 | 3.6 | 3.1 | 2.2 | 1.3 | — | — | — | — |
| EMU02 | 0.47 | 0.28 | 0.17 | 0.15 | 0.14 | 0.12 | 0.007 | 0.05 | — |
| | 8.7 | 5.5 | 3.5 | 3.4 | 3.3 | 2.7 | 2.0 | 1.6 | — |

—=crystallization of the aqueous phase

It can be seen that the stability of the emulsion increases as the temperature decreases, to the point at which it breaks due to crystallization of the water and the paraffins.

EXAMPLE 6

In this example, the stability of the emulsion at a temperature of 70° C. is studied. During the first step of the process, the temperature of the emulsion is gradually increased, at a rate of 1° C./min, until the 70° C. steady stage is reached. The measurements carried out continuously on the apparent weight of the crucible allow the curve in FIG. 5 to be established.

Firstly, during the first step, a substantial increase in weight due essentially to a decrease in the density of the hydrocarbon fraction of the emulsion is observed. Next, a non-linear change (AB uniformly accelerated) in the relative weight is observed, due to demixing of the water present in the composition of the emulsion, up to the point of total phase separation.

What is claimed is:

1. A process for determining the stability of a water-hydrocarbon emulsion, comprising the steps of:
   (A) heating said emulsion, thereby raising a temperature of said emulsion to a predetermined test temperature;
   continuously measuring by thermogravimetry the variation in the apparent weight P of a gravimetric detector, a portion of which is immersed in the emulsion;
   (B) maintaining said test temperature of said emulsion while continuously measuring the variation in the apparent weight of the said detector by thermogravimetry, and simultaneously recording a measurement curve of said variation;
   collecting a mass of a separated phase; and
   determining from the said curve the speed of separation of phases corresponding to the slope of the said curve;
   wherein the speed measured at the breaking point corresponds to a substantial and continuous increase in the apparent weight P at the start of step (B);
   deducing the stability of the emulsion by comparison of said measured at the breaking point with a speed of a reference emulsion.

2. The process according to claim 1, wherein the predetermined test temperature is between 10 to 70° C. and wherein the emulsion is adjusted to said test temperature starting from ambient temperature at a heating speed or cooling speed of between 0.05 and 10° C./min.

3. The process according to claim 1, wherein the predetermined test temperature is between the crystallization temperature of water and that of a paraffin contained in said emulsion; and
   wherein the emulsion is adjusted to the test temperature by accelerated cooling at a rate of between 0.05 to 10° C./min.

4. The process according to claim 1, wherein the predetermined test temperature is less than the crystallization temperatures of a paraffin contained in said emulsion and of an aqueous phase, but greater than the flow point of the water-hydrocarbon emulsion; and
   wherein the emulsion is adjusted to the test temperature at a cooling rate of between 0.05 and 10° C./min.

5. The process according to claim 1, wherein said emulsion comprises an additive which promotes the maintenance of a homogeneity of a liquid emulsion.

6. The method according to claim 1, wherein said water-hydrocarbon emulsion comprises an emulsified fuel.

7. A device for the thermogravimetric separation of an emulsion into an aqueous phase and a hydrocarbon-based liquid phase, comprising:
   a thermogravimetric balance fitted with a gravimetric detector having a crucible which is immersed in a tank containing said emulsion;

wherein said tank is connected to a cooling circuit;

wherein said crucible is freely suspended in said emulsion;

wherein the tank has a cylindrical cross section so that the ratio of the largest diameter of the crucible to a diameter of the tank is between 0.1 and 0.9.

8. The device according to claim 7, wherein the crucible is coaxially suspended.

9. The device according to claim 7, wherein the crucible has a cylindrical shape comprising a base and a rim;

wherein the height of the rim is between 5 mm and 30 mm.

10. The device according to claim 9, wherein the height of the rim is 5 mm.

* * * * *